United States Patent
Olson et al.

(10) Patent No.: US 9,638,669 B2
(45) Date of Patent: May 2, 2017

(54) PORTABLE FUEL DILUTION METER AND METHOD

(71) Applicant: Spectro Scientific, Inc., Chelmsford, MA (US)

(72) Inventors: Eric J. Olson, Phillipston, MA (US); Henry Wohltjen, Bowling Green, KY (US); Yuegang Zhao, Andover, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 331 days.

(21) Appl. No.: 14/458,476

(22) Filed: Aug. 13, 2014

(65) Prior Publication Data

US 2016/0047779 A1    Feb. 18, 2016

(51) Int. Cl.
    *G01N 29/02*    (2006.01)

(52) U.S. Cl.
    CPC ... *G01N 29/022* (2013.01); *G01N 2291/0256* (2013.01); *G01N 2291/0423* (2013.01)

(58) Field of Classification Search
    CPC .... Y02E 60/50; H01M 8/04156; B60K 13/04; B60K 1/00; B60K 1/04; G01N 29/02; G01N 29/022; G01N 2291/0423; G01N 2291/0256
    USPC ........................................................ 73/24.01
    See application file for complete search history.

(56) References Cited

U.S. PATENT DOCUMENTS

| | | | | |
|---|---|---|---|---|
| 4,045,139 A | * | 8/1977 | Russ | G01N 33/2835 356/36 |
| 5,200,064 A | * | 4/1993 | Russ | G01N 33/2829 210/236 |
| 5,229,295 A | * | 7/1993 | Travis | G01N 31/222 436/166 |
| 5,465,608 A | | 11/1995 | Lokshin et al. | |
| 5,469,369 A | | 11/1995 | Rose-Pehrsson et al. | |
| 8,361,675 B2 | * | 1/2013 | Jufuku | B60K 13/04 180/65.1 |
| 8,649,009 B2 | | 2/2014 | Bohle | |
| 2007/0007194 A1 | * | 1/2007 | Yoshida | B60K 1/00 210/359 |

* cited by examiner

*Primary Examiner* — Eric S McCall
*Assistant Examiner* — Mohammed E Keramet-Amircola
(74) *Attorney, Agent, or Firm* — Iandiorio Teska & Coleman, LLP (57) ABSTRACT

A portable fuel dilution meter and method includes a plurality of sample bottles each with a lid securable thereto and an absorbent material in the bottle. A housing includes a sample bottle receptacle and a hinged head unit over the receptacle including at least a first needle piercing the lid of a sample bottle loaded into the housing receptacle and extending into the headspace of the sample bottle when the head is closed. A vapor sensor is fluidly coupled to the first needle for analyzing vapors in the headspace of the sample bottle.

23 Claims, 8 Drawing Sheets

PORTABLE FUEL DILUTION METER AND METHOD

FIELD OF THE INVENTION

The subject invention relates to vapor sensing devices and fuel dilution meters.

BACKGROUND OF THE INVENTION

Vapor sensing devices using a surface acoustic wave (SAW) sensor are known. See for example U.S. Pat. Nos. 5,469,369, and 5,465,608 incorporated herein by this reference.

Such devices can be used in systems to detect the presence of a contaminant (e.g., fuel, moisture, or a coolant) in oil (e.g., engine oil, hydraulic oil, or the like). The fuel dilution meter (Q600) product available from Spectro Scientific, Inc. (Chelmsford, Mass.) is an example of such a system.

In that system, a rather large bottle is filled ⅔ full with oil and inserted into the machine. A tube is inserted into the bottle. Vapors in the "headspace" of the bottle above the oil are drawn via the tube and a pump over a SAW sensor module which detects the presence of contaminant vapors.

But, if the bottle is filled too full, liquid oil can be drawn into the instrument and damage the SAW sensor. Also, oil can contaminate the tube, the vapor inlet, the sample stand, and/or other components of the system resulting in erroneous readings.

Finally, this test method is very sensitive to oil temperature under test. Due to the high oil volume it takes a long time to cool down the oil sample if oil was freshly collected from a warm or hot engine. Error occurs when sample is not tested at the same temperature as the calibration samples are tested.

Moreover, the current system is not portable and requires the sample to be delivered to a laboratory for analysis.

SUMMARY OF THE INVENTION

In some aspects, provided is a portable fuel dilution meter which is easy to use on site, quick and reliable. Sampling is consistent between samples and the chance of contamination of the meter is reduced. New disposable sample bottles require only a small amount of fluid to be sampled (e.g., 1 ml) and an absorbent material in each sample bottle provides a consistent surface area for vapor build up in the sample bottle headspace as well a heat sink to cool oil samples quickly to room temperature. In some designs, greater range and stability are provided and accuracies of 0.2% wt. with a range of 15% are provided. Up to three stored calibrations can be included to properly sample and detect diesel in oil, gasoline in oil, JP8 fuel in hydraulic oil, and the like. One preferred device is battery operated and uses rechargeable batteries for transportability. A preferred portable fuel dilution meter samples at a rate of approximately 20 seconds per sample. A USB connection may be included for data transfer.

Featured is a portable fuel dilution meter comprising a plurality of sample bottles each with a lid securable thereto and an absorbent material in the bottle. A housing includes a receptacle for a bottle. A hinged head unit over the sample bottle receptacle includes at least a first needle piercing the lid of a sample bottle loaded into the housing receptacle and extending into the headspace of the sample bottle when the head unit is closed. A vapor sensor is fluidly coupled to the first needle for analyzing vapors in the headspace of the sample bottle delivered to the vapor sensor. There may be a heater in the receptacle. Further, the sample bottle can be pressurized by the meter pump(s).

The hinged head unit may further include a second needle piercing the lid of the sample bottle when the head is closed for allowing ambient air into the headspace of the sample bottle. The absorbent material preferably includes a felt disk disposed at the bottom of each sample bottle. Each felt disk for each bottle is configured the same and each bottle is configured the same.

The vapor sensor is preferably a surface acoustic wave sensor. The meter may further include a mechanism for releasably locking the hinged head unit in a closed position. In one design, a clip is provided and a magnet and an adjustable set screw cooperate to retain the head unit in a closed position which can be adjusted relative to the sample bottle lid.

Also featured is a detection method comprising disposing one to a few milliliters of fluid into a sample bottle, absorbing the fluid in an absorbent material within the sample bottle, securing a lid onto the sample bottle, placing the sample bottle in a sample bottle receptacle, piercing the sample bottle lid with a first needle, directing vapor in the sample bottle through the needle to a vapor sensor, and analyzing the vapor.

Piercing the lid with the first needle may include closing a hinged head unit including the first needle down over the sample bottle receptacle. The hinged head unit may further include a second needle piercing the lid of the sample bottle when the head is closed for allowing ambient air into the headspace of the sample bottle.

The absorbent material may include a felt disk disposed at the bottom of each sample bottle. Preferably, each felt disk for each bottle is configured the same and each bottle is configured the same. Example disks have diameters on the order of 12 mm, a thickness of 1 mm, and a microstructure and pore volume consistent with pressed wool. Analyzing the vapor may include directing the vapor to a surface acoustic wave sensor.

Also featured is a method of detecting fuel dilution. One preferred method includes disposing one to a few milliliters of oil into a sample bottle, absorbing the oil in an absorbent material disposed within the sample bottle, securing a lid onto the sample bottle, placing the sample bottle in a fuel dilution meter sample bottle receptacle, piercing the sample bottle lid with a first needle, and directing vapor in the sample bottle through the needle to a SAW sensor.

A plurality of sample holders for a fuel dilution meter are each preferably configured the same and include a bottle with an open end and a pierceable lid releasably coupled to the bottle open top end. A vapor headspace in the bottle is below the pierceable lid. An absorbent material in the bottle below the vapor headspace absorbs a fluid placed in the bottle and releases vapors into the bottle headspace. The absorbent material may include a felt disk disposed at the bottom of each sample bottle. Preferably, each felt disk for each bottle is configured the same and each bottle is configured the same.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
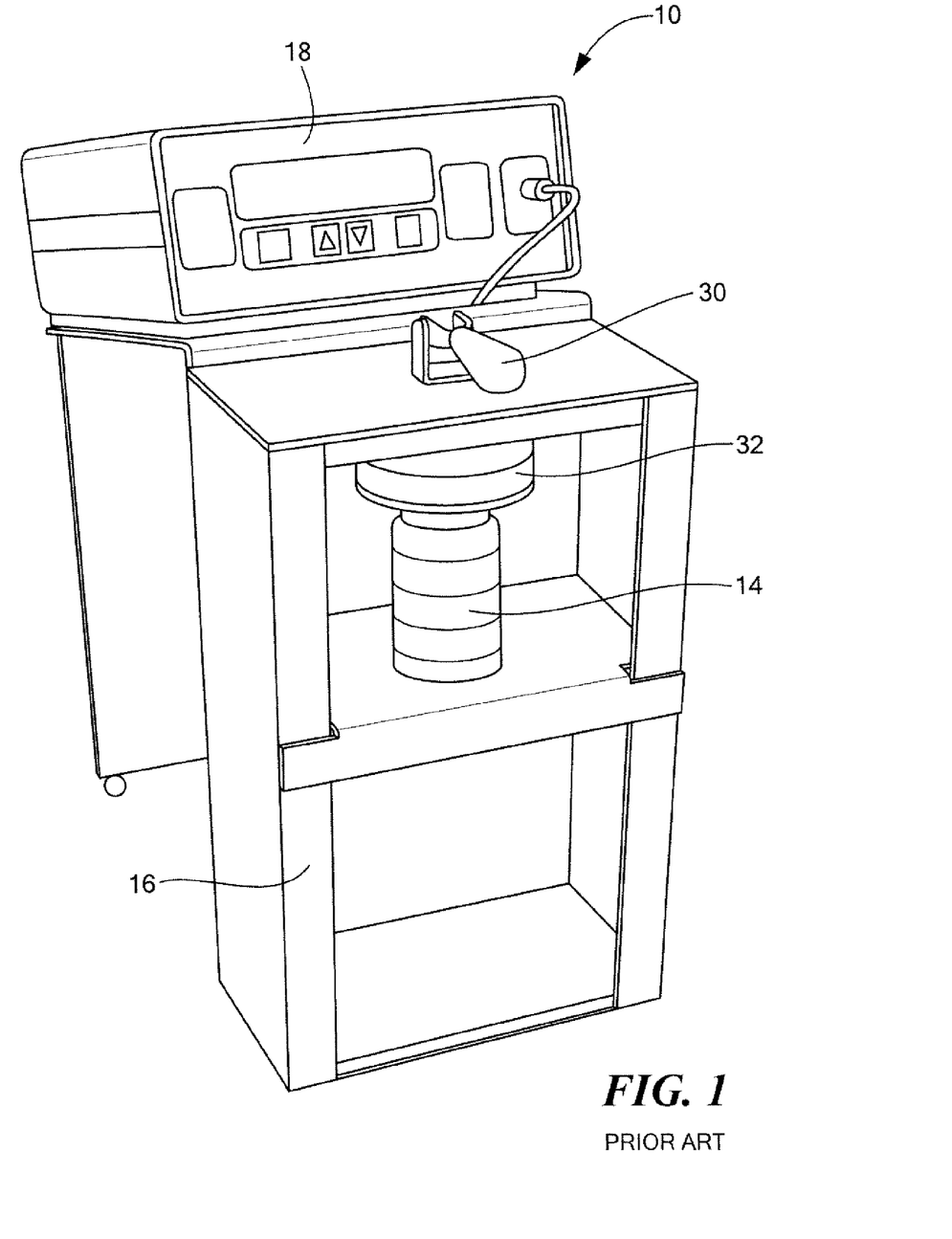
FIG. 1 is a schematic front view of a prior art fuel dilution meter.

FIG. 1 shows a prior art laboratory fuel dilution measurement apparatus 10 where large bottle 14 is filled ¾ full with crank case oil and placed in stand 16. Electronic module 18 includes SAW sensor module 20, FIG. 2 providing an output signal to data acquisition and control microprocessor 22 for detecting the type of vapors in the headspace 24 above the oil 26 level in bottle 14. In this way, contaminants such as fuel and the like in the oil can be detected.

Figure 2:
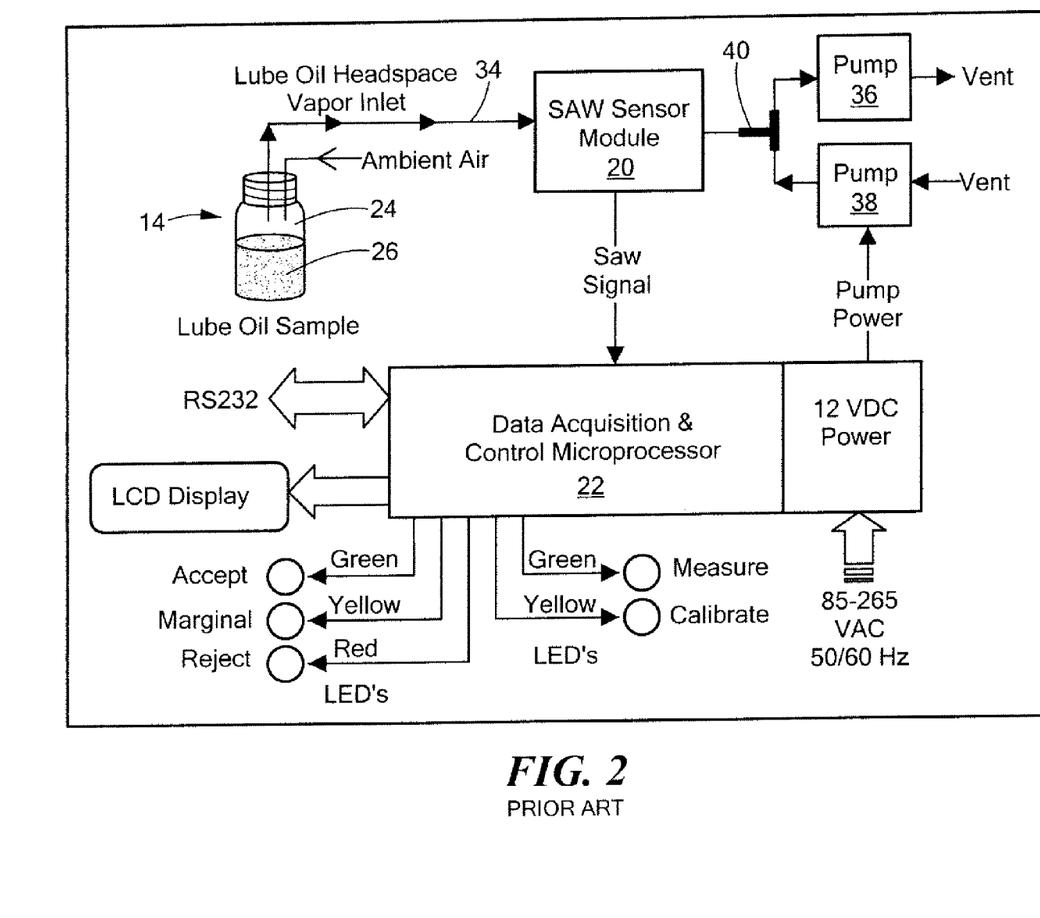
FIG. 2 is a block diagram showing the primary components associated with the fuel dilution meter of FIG. 1.

Handle 30, FIG. 1 brings gasket 32 into engagement onto the open top end of bottle 14 and line 34, FIG. 2 delivers vapor to SAW sensor 20 via pump 36. Purge pump 38 and valve 40 may also be included.

As noted in the Background section above, oil, gas, or the like can contaminate gasket 32, FIG. 1, line 34, FIG. 2, and/or other components of the system resulting in unreliable readings. Also, if the bottle 14 is filled too full, liquid can be delivered to SAW sensor module 20 damaging it.

It was found, for example, that if a first sample of oil with 5% fuel was tested and touched the meter gasket 32 and then a second sample of oil with 1% fuel was tested, the sensor inaccurately reported that the second sample of oil had 2.5% fuel do to the presence of some of the first oil sample still on or in the meter.

Figure 3:
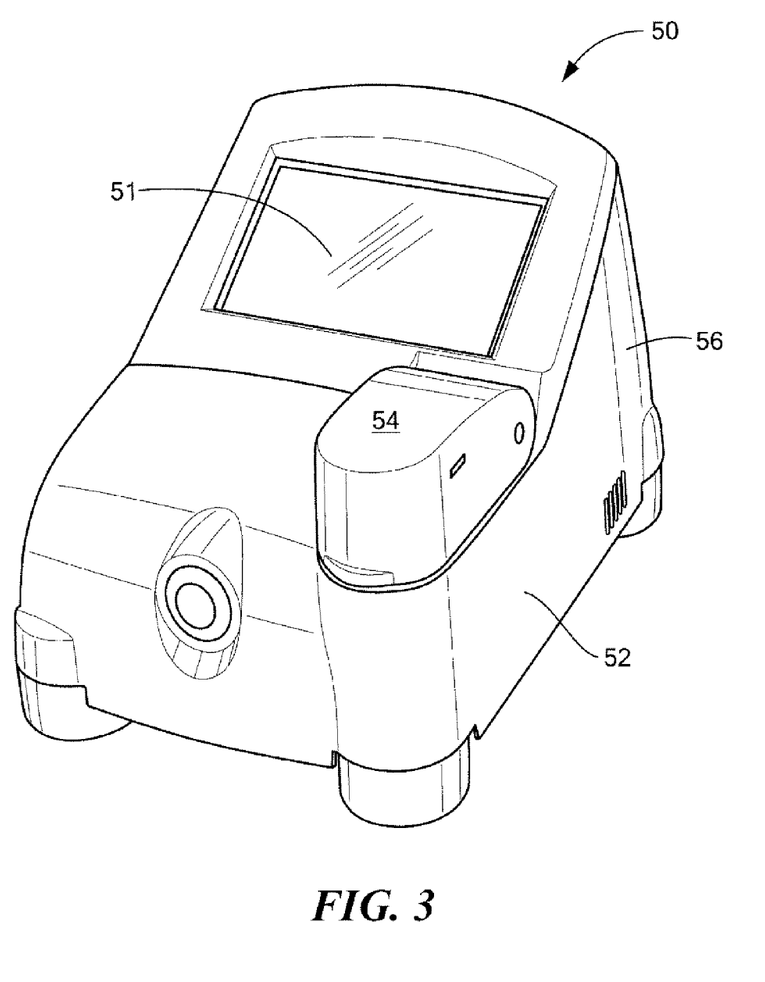
FIGS. 3-4 are schematic front views showing a portable fuel dilution meter in accordance with an example of the subject invention.

FIG. 3 shows an example of a new portable fuel dilution meter 50 with housing 52 preferably enclosing an electronic subsystem the same as or similar to that depicted in FIG. 2. Preferably, this portable fuel dilution meter is light weight, small in size, and powered by a lithium ion rechargeable battery via a universal charger. Touch screen 51 displays the results of an analysis and can be used as an input device. A range of 0.2% to 15% is featured as is an accuracy of 0.2%.

Figure 4:
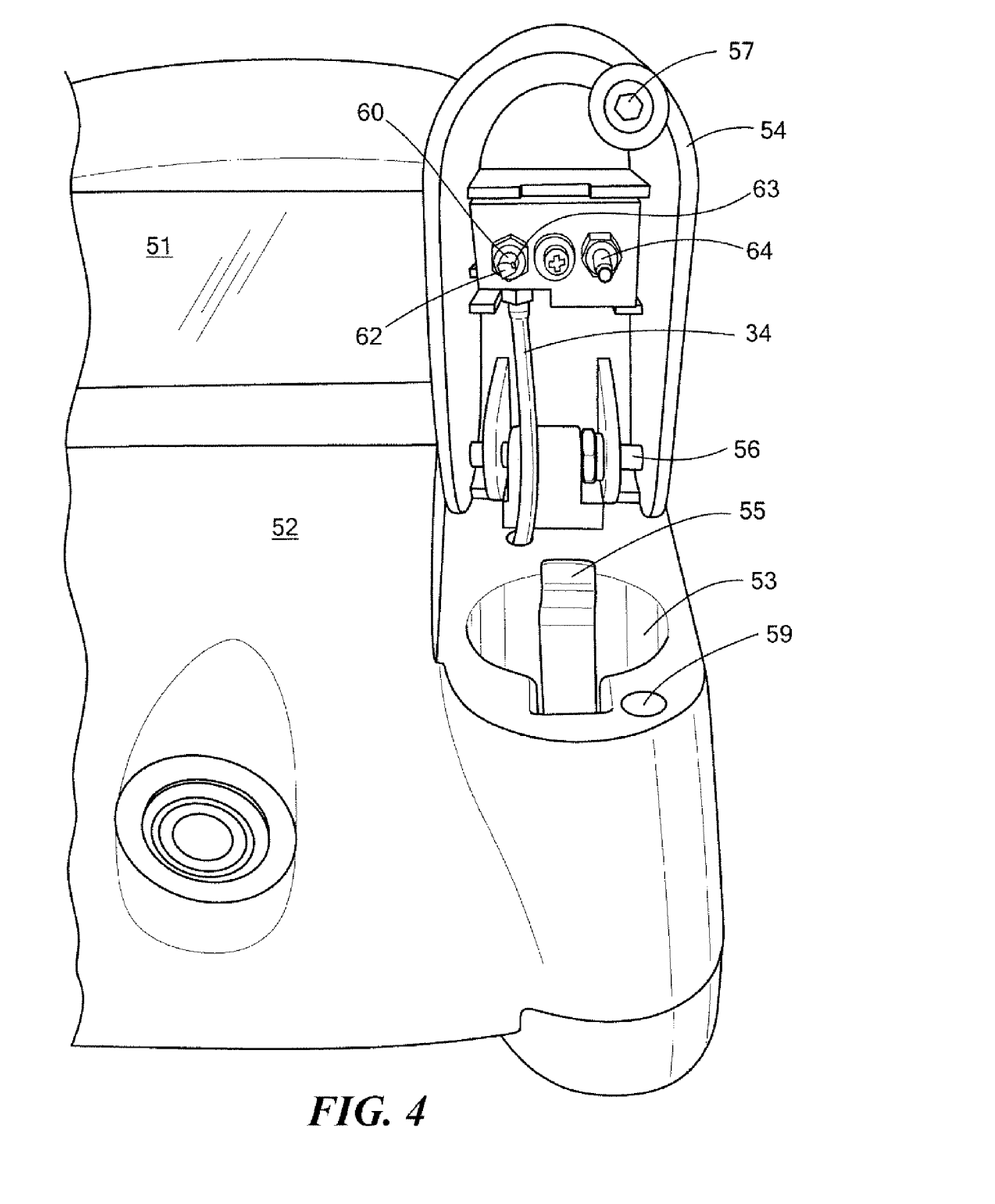

Head unit 54 is hinged to the housing via pin 56 over sample bottle receptacle 53, FIG. 4 in the housing. Clip 55 retains head unit in the closed position. Adjustable set screw 57 on head unit 54 cooperates with magnet 59 on base unit 52 to retain the head unit in the closed position and for spacing adjustment so the needles 60 and 64 properly pierce the sample bottle plastic lid without head unit 54 putting too much pressure on the sample bottle lid.

Figure 5:
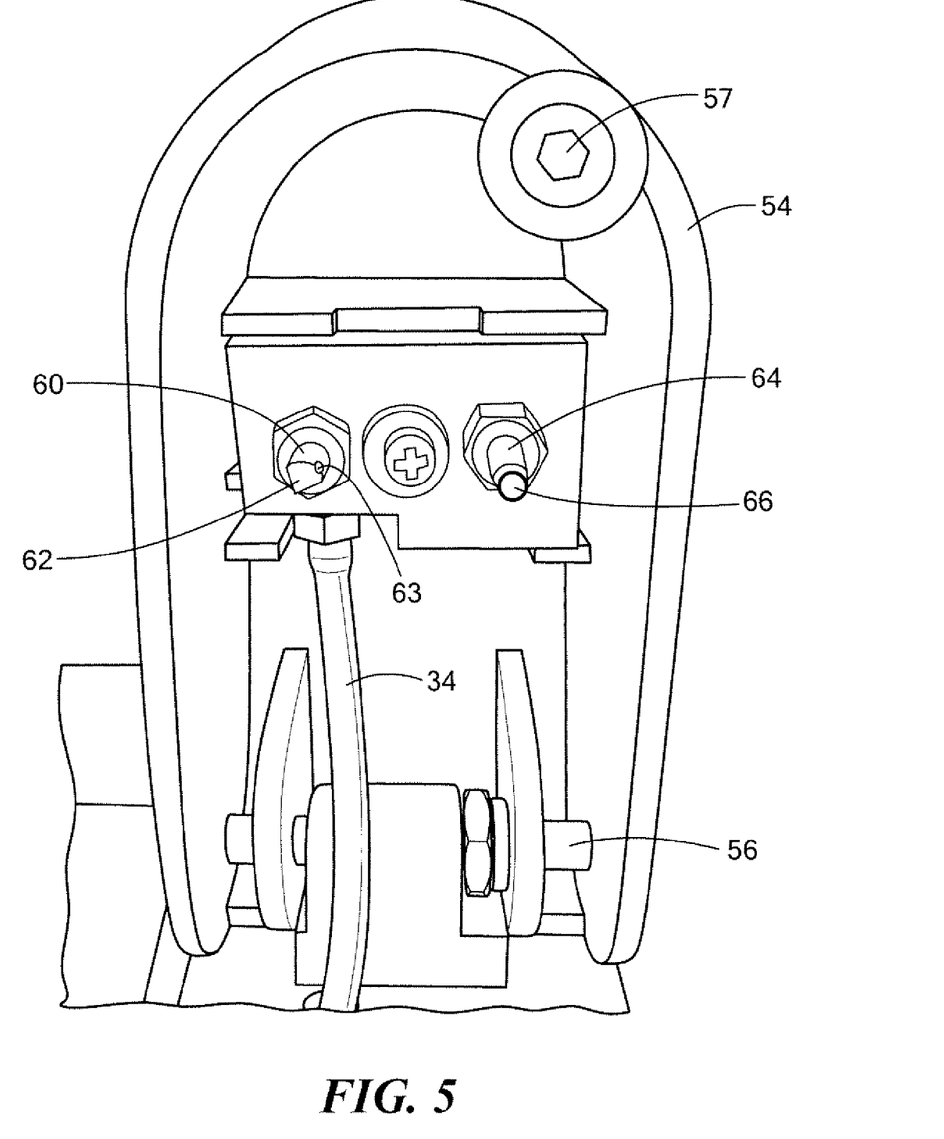
FIG. 5 is a schematic view showing the sample bottle lid piercing needles of the portable fuel dilution meter hinged head unit.

FIG. 5 also shows head unit first needle 60 with a solid pointed tip 62 and side vapor orifice 63. Needle 60 is used to pierce the lid of a sample bottle and to draw vapor present in the headspace of the sample bottle via orifice 63 and through a conduit 34 connected to needle 60 to a vapor sensor such as depicted in FIG. 2. Head needle 64 with a distal bottom opening 66 pierces the sample bottle lid and supplies ambient air into the sample bottle. Needles 60 and 64 may be retained in block 65.

Figure 6A:
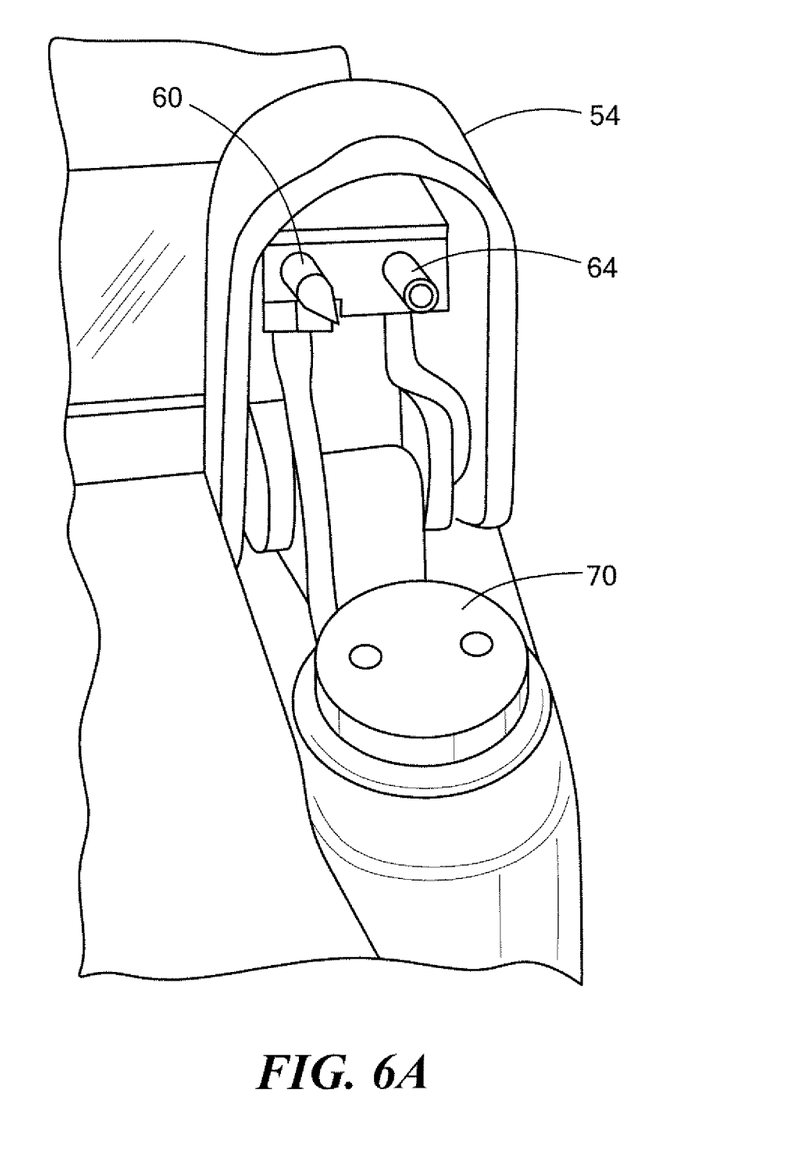
FIG. 6A is a schematic view showing a sample bottle placed in the portable fuel dilution meter.
Figure 6B:
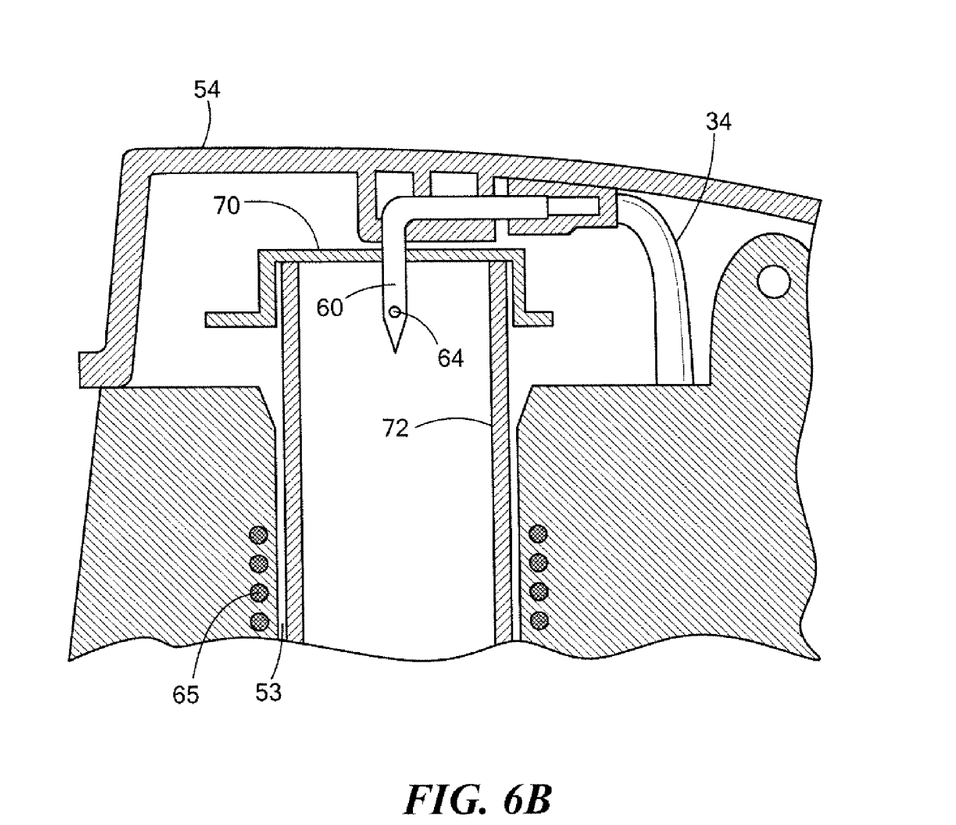
FIG. 6B is a schematic cross sectional view showing a sample bottle disposed in the portable fuel dilution meter and the vapor delivery needle piercing the sample bottle lid.

FIGS. 6A and 6B show sample bottle 72 and pierceable lid 70 loaded into the device receptacle. Conduit 34 (e.g., a tube) is also shown for delivering vapor to a vapor sensor system such as a SAW sensor. The pump used (see FIG. 2) can be operated to pressurize sample bottle 72 via needle 60 to assist in vapor development. Further, receptacle 53 may include a heater coil 65 to control the temperature of the sample bottle in order to ensure a consistent vapor release. Because the sample is low volume, it quickly reaches room temperature. Heater coil 65 can maintain the bottle at consistent temperatures dispute different ambient temperatures.

Figure 7:
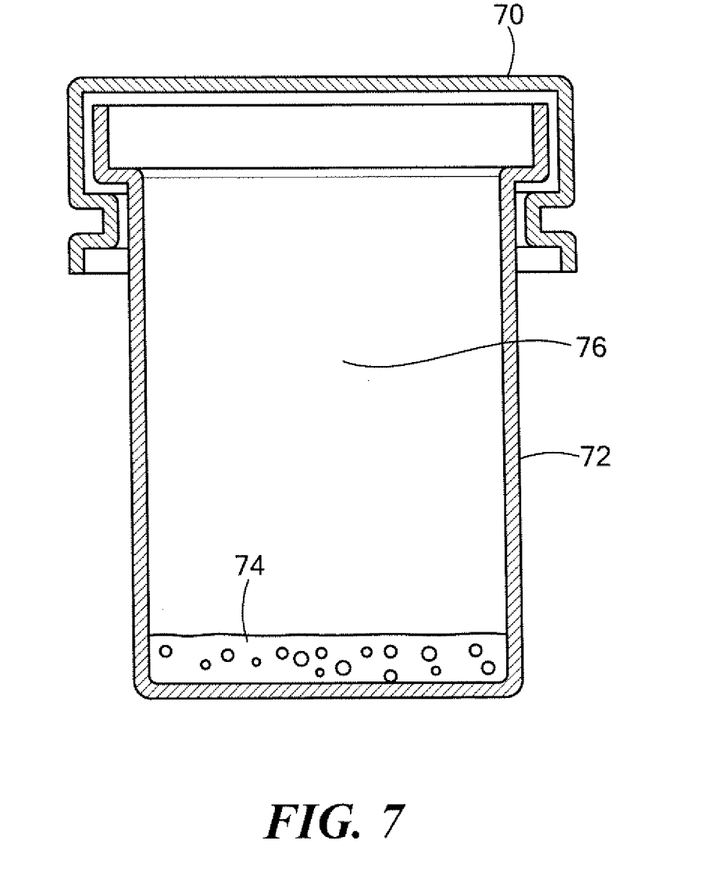
FIG. 7 is a schematic cross section view showing an example of a disposable sample bottle in accordance with examples of the invention.

In one preferred design, sample bottle 72, FIG. 7, and pierceable lid 70 are made of plastic and lid 70 snap fits onto the upper open end of the sample bottle. One bottle was approximately 2 inches tall and approximately 1 inch in diameter. FIG. 7 also shows absorbent material 74, e.g., a disk of felt material disposed at the bottom of the sample bottle. Each sample bottle and each disk of absorbent material are preferably configured the same to absorb the sample oil and release the same amount of vapor into the large headspace 76 in the sample bottle between the absorbent disk and the lid of the bottle. That is, each sample bottle is the same size and each absorbent disk is the same diameter, thickness, and has the same microstructure and pore volume. Example disks have diameters on the order of 12 mm, a thickness of 1 mm, and a microstructure and pore volume consistent with pressed wool. Lambs wool may be used as the absorbent disk.

In use, a small amount of crank case oil (e.g., one half a milliliter to a few milliliters) is pipetted into the bottle 72 and is absorbed by absorbent disk 74. Lid 70 is then secured to the sample bottle top. The sample bottle is then loaded into the meter receptacle 53, FIG. 4 and head 54, FIG. 3-6 is pushed down whereupon needles 60 and 64 pierce the sample bottle lid. Vapor is then delivered from the sample bottle headspace to the vapor sensor for analysis. The bottle and the pierced lid are then removed from the machine and discarded.

In this way, the chance of contamination of the meter with oil or other contaminants is reduced and oil analysis is simplified. If the sample bottle is tipped or even dropped, no oil can leak out because it is absorbed in the absorbent disk.

Note that in the prior art (FIGS. 1-2) bottle 14 is rather large and a large quantity of oil is dispensed into the bottle. There is no bottle lid. Spillage of the oil is a problem as is possible contamination of the meter. It was found that the sample stand was easily contaminated. Further, in the prior art, it took a long time to establish equilibrium in the headspace of the sample bottle. Only a single calibration was possible and the meter was not usable in the field.

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:
1. A portable fuel dilution meter comprising:
a housing including a receptacle for a bottle;
a head unit over the receptacle including at least a first needle piercing the lid of a sample bottle loaded into the housing receptacle and extending into the headspace of the sample bottle when the head unit is closed; and
a vapor sensor fluidly coupled to the first needle for analyzing vapors in the headspace of the sample bottle delivered to the vapor sensor.
2. The meter of claim 1 in which the head unit further includes a second needle piercing the lid of the sample bottle when the head is closed for allowing ambient air into the headspace of the sample bottle.
3. The meter of claim 1 further including a pump for pressurizing the sample bottle via the first needle.
4. The meter of claim 1 wherein the receptacle includes a heater to control the temperature of the sample bottle.
5. The meter of claim 1 further including a plurality of sample bottles each with a lid securable thereto and an absorbent material in the bottle.
6. The meter of claim 5 in which the absorbent material includes a felt disk disposed at the bottom of each sample bottle.
7. The meter of claim 6 in which each felt disk for each bottle is configured the same and each bottle is configured the same.
8. The meter of claim 1 in which the vapor sensor is a surface acoustic wave sensor.
9. The meter of claim 1 further includes a mechanism for releasably locking the hinged head unit in a closed position.
10. The meter of claim 9 in which said mechanism includes a clip.
11. The meter of claim 9 in which said mechanism includes a magnet and an adjustable set screw cooperating with the magnet.
12. The meter of claim 1 in which the head unit includes a hinge.
13. A detection method comprising:
disposing a small amount of fluid into a sample bottle;
absorbing said fluid in an absorbent material within the sample bottle;
securing a lid onto the sample bottle;
placing the sample bottle in a sample bottle receptacle;
piercing the sample bottle lid with a first needle;
directing vapor in the sample bottle through the needle to a vapor sensor; and
analyzing said vapor.
14. The method of claim 13 in which piercing the lid with the first needle includes closing a hinged head unit including said first needle down over the sample bottle receptacle.
15. The method of claim 14 in which the hinged head unit further includes a second needle piercing the lid of the sample bottle when the head is closed for allowing ambient air into the headspace of the sample bottle.
16. The method of claim 13 in which the absorbent material includes a felt disk disposed at the bottom of each sample bottle.
17. The method of claim 16 in which each felt disk for each bottle is configured the same and each bottle is configured the same.
18. The method of claim 13 in which analyzing the vapor includes directing the vapor to a surface acoustic wave sensor.
19. A method of detecting fuel dilution, the method comprising:
disposing a small amount of oil into a sample bottle;
absorbing the oil in an absorbent material disposed within the sample bottle;
securing a lid onto the sample bottle;
placing the sample bottle in a fuel dilution meter sample bottle receptacle;
piercing the sample bottle lid with a needle; and
directing vapor in the sample bottle through the needle to a SAW sensor.
20. A plurality of sample holders for a fuel dilution meter, each holder configured the same and comprising:
a bottle with an open end;
a pierceable lid releasably coupled to the bottle open end;
a vapor headspace in the bottle below the pierceable lid; and
an absorbent material in the bottle below the vapor headspace absorbing a fluid placed in the bottle and releasing vapors into the bottle headspace.
21. The holder of claim 20 in which the absorbent material includes a felt disk disposed at the bottom of each sample bottle.
22. The holder of claim 21 in which each felt disk for each bottle is configured the same and each bottle is configured the same.
23. The holder of claim 22 in which each felt disk is approximately 12 mm in diameter and approximately 1 mm thick.

* * * * *